US010294284B2

(12) United States Patent
Thielens et al.

(10) Patent No.: US 10,294,284 B2
(45) Date of Patent: May 21, 2019

(54) METHOD FOR PREPARING C1Q RECOMBINANT PROTEIN

(71) Applicants: COMMISSARIAT A L'ENERGIE ATOMIQUE ET AUX ENERGIES ALTERNATIVES, Paris (FR); INSTITUT NATIONAL DE LA SANTE ET DE LA RECHERCHE MEDICALE (INSERM), Paris (FR)

(72) Inventors: Nicole Thielens, St Blaise du Buis (FR); Isabelle Bally, Fontanil Cornillon (FR)

(73) Assignees: COMMISSARIAT A L'ENERGIE ATOMIQUE ET AUX ENERGIES ALTERNATIVES, Paris (FR); INSTITUT NATIONAL DE LA SANTE DE LA RECHERCHE MEDICALE (INSERM), Paris (FR)

( * ) Notice: Subject to any disclaimer, the term of this patent is extended or adjusted under 35 U.S.C. 154(b) by 30 days.

(21) Appl. No.: 14/434,385

(22) PCT Filed: Oct. 9, 2013

(86) PCT No.: PCT/IB2013/059236
§ 371 (c)(1),
(2) Date: Apr. 8, 2015

(87) PCT Pub. No.: WO2014/057437
PCT Pub. Date: Apr. 17, 2014

(65) Prior Publication Data
US 2015/0329606 A1 Nov. 19, 2015

(30) Foreign Application Priority Data
Oct. 9, 2012 (FR) ..................... 12 59635

(51) Int. Cl.
| C07K 1/00 | (2006.01) |
| C07K 14/00 | (2006.01) |
| C07K 17/00 | (2006.01) |
| C12P 21/06 | (2006.01) |
| C12N 1/20 | (2006.01) |
| C12N 15/00 | (2006.01) |
| C12N 5/071 | (2010.01) |
| C07H 21/04 | (2006.01) |
| C07K 14/47 | (2006.01) |

(52) U.S. Cl.
CPC ............ C07K 14/47 (2013.01); C07K 14/472 (2013.01); *C07K 2319/43* (2013.01); *C07K 2319/50* (2013.01)

(58) Field of Classification Search
CPC .......................... A61K 38/1725; C07K 14/472
See application file for complete search history.

(56) References Cited

PUBLICATIONS

Bally et al. "Expression of recombinant human complement C1q allows identification of the C1r/C1s-binding sites" Proc. Natl. Acad. Sci. 110:8650-8655. Published May 21, 2013.*
Origene "C1QC (NM_172369) Purified Human Protein" Catalog No. TP303832. Published May 16, 2012.*
Kojourharova et al. "Mutation Analyses of the Recombinant Globular Regions of Human C1q A, B, and C Chains Suggest an Essential Role for Arginine and Histidine Residues in the C1q-IgG Interation" J Immunol 172:4351-4358. Published 2004.*
Origene "C1QC (NM_172369) Human cDNA ORF Clone" Catalog No. RC203832. Published May 4, 2011.*
Zhang et al. "Influenza A virus M1 blocks the classical complement pathway through interacting with C1qA" J. Gen. Virol. 90:2751-2758. Published 2009.*
Li et al. "Tumor Necrosis Factor Death Receptor Signaling Cascade is Required for Amyloid-Beta Protein-Induced Neuron Death" J. Neurosci. 24:1760-1771. Published 2004.*
Romier et al. "Co-expression of protein complexes in prokaryotic and eukaryotic hosts: experimental procedures, database tracking and case studies" Acta Cryst. D62:1232-1242. Published 2006.*
Kriz et al. "Integration of multiple expression cassettes into mammalian genomes in a single step" Protocol Exchange doi:10.103/protex.2011.249. (Year: 2011).*
Assur et al. "Tools for Coproducing Multiple Proteins in Mammalian Cells", Chapter 12 in Protein Expression in Mammalian Cells: Methods and Protocols, Methods in Molecular Biology 801:173-187. (Year: 2011).*
"C1QC (NM 172369) Purified Human Protein", Origene, product catalog, cat. No. TP303832, May 16, 2012 (May 16, 2012), pp. 1-1, XP002697854, Retrieved from the Internet on May 29, 2013.
"C1QC Over-expression Lysate Product", Origene, product catalog, cat. No. LY403541, May 4, 2011 (May 4, 2011), p. 1, XP002697855, Retrieved from the Internet on May 29, 2013.
"C1QC (NM 172369) Human cDNA ORE Clone", Origene, product catalog, cat. No. RC203832 May 4, 2011 (May 4, 2011), p. 1, XP002697856, Retrieved from the Internet on May 29, 2013.
"ORE nucleotide sequence for C1QC human cDNA clone, cat. No. RC203832", May 4, 2011 (May 4, 2011), XP002697857, Retrieved from the Internet on May 29, 2013.
"Protein sequence of C1QC human cDNA clone, cat. No. RC203832", May 4, 2011 (May 4, 2011), XP002697858, Retrieved from the Internet on May 29, 2013.
J. Zhang et al: "Influenza A virus M1 blocks the classical complement pathway through interacting with ClqA", Journal of General Virology, vol. 90, No. 11, Nov. 1, 2009 (Nov. 1, 2009), pp. 2751-2758.

(Continued)

*Primary Examiner* — Zachary J Miknis
(74) *Attorney, Agent, or Firm* — Arrigo, Lee, Guttman & Mouta-Bellum LLP

(57) ABSTRACT

The present invention relates to a method for recombinant production of a C1q protein or a variant of the C1q protein, in which the protein is recovered from an in vitro culture of cells expressing a C1qA subunit or a variant of the C1qA subunit, a C1qB subunit or a variant of the C1qB subunit, and a C1qC subunit or a variant of the C1qC subunit, in which at least one of the subunits or subunit variants also has at the N-terminus or C-terminus a sequence of amino acids of at least six residues, at least 40% of which are glutamic acid and/or aspartic acid residues.

5 Claims, 4 Drawing Sheets

Specification includes a Sequence Listing.

(56)     References Cited

PUBLICATIONS

R. Li et al: "Tumor Necrosis Factor Death Receptor Signaling Cascade is Required for Amyloid-Protein-Induced Neuron Death", Journal of Neuroscience, vol. 24, No. 7, Feb. 18, 2004 (Feb. 18, 2004), pp. 1760-1771.

Gaboriaud Christine et al: "The crystal structure of the globular head of complement protein C1q provides a basis for its versatile recognition properties", Journal of Biological Chemistry, American Society for Biochemistry and Molecular Biology, US, vol. 278, No. 47, Nov. 21, 2003 (Nov. 21, 2003), pp. 46974-46982.

International Search Report of PCT/IB2013/059236, dated Apr. 7, 2014.

Isabelle Bally, et al., "Expression of recombinant human complement C1q allows identification of the C1r/C1s-binding sites," PNAS, vol. 110, No. 21, pp. 8650-8655 (2013).

\* cited by examiner

SEQUENCE LISTING

<160> NUMBER OF SEQ ID NOS: 24

<210> SEQ ID NO 1
<211> LENGTH: 223
<212> TYPE: PRT
<213> ORGANISM: Homo sapiens

<400> SEQUENCE: 1

```
Glu Asp Leu Cys Arg Ala Pro Asp Gly Lys Lys Gly Glu Ala Gly
1               5                   10                  15

Pro Gly Arg Arg Gly Arg Pro Gly Leu Lys Gly Glu Gln Gly Glu Pro
            20                  25                  30

Gly Ala Pro Gly Ile Arg Thr Gly Ile Gln Gly Leu Lys Gly Asp Gln
        35                  40                  45

Gly Glu Pro Gly Pro Ser Gly Asn Pro Gly Lys Val Gly Tyr Pro Gly
    50                  55                  60

Pro Ser Gly Pro Leu Gly Ala Arg Gly Ile Pro Gly Ile Lys Gly Thr
65                  70                  75                  80

Lys Gly Ser Pro Gly Asn Ile Lys Asp Gln Pro Arg Pro Ala Phe Ser
                85                  90                  95

Ala Ile Arg Arg Asn Pro Pro Met Gly Gly Asn Val Val Ile Phe Asp
            100                 105                 110

Thr Val Ile Thr Asn Gln Glu Glu Pro Tyr Gln Asn His Ser Gly Arg
        115                 120                 125

Phe Val Cys Thr Val Pro Gly Tyr Tyr Tyr Phe Thr Phe Gln Val Leu
    130                 135                 140

Ser Gln Trp Glu Ile Cys Leu Ser Ile Val Ser Ser Arg Gly Gln
145                 150                 155                 160

Val Arg Arg Ser Leu Gly Phe Cys Asp Thr Thr Asn Lys Gly Leu Phe
                165                 170                 175

Gln Val Val Ser Gly Gly Met Val Leu Gln Leu Gln Gln Gly Asp Gln
            180                 185                 190

Val Trp Val Glu Lys Asp Pro Lys Lys Gly His Ile Tyr Gln Gly Ser
        195                 200                 205

Glu Ala Asp Ser Val Phe Ser Gly Phe Leu Ile Phe Pro Ser Ala
    210                 215                 220
```

<210> SEQ ID NO 2
<211> LENGTH: 245
<212> TYPE: PRT
<213> ORGANISM: Homo sapiens

<400> SEQUENCE: 2

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140
```

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245

<210> SEQ ID NO 3
<211> LENGTH: 228
<212> TYPE: PRT
<213> ORGANISM: Homo sapiens

<400> SEQUENCE: 3

Gln Ala Gln Leu Ser Cys Thr Gly Pro Pro Ala Ile Pro Gly Ile Pro
1               5                   10                  15

Gly Ile Pro Gly Thr Pro Gly Pro Asp Gly Gln Pro Gly Thr Pro Gly
            20                  25                  30

Ile Lys Gly Glu Lys Gly Leu Pro Gly Leu Ala Gly Asp His Gly Glu
        35                  40                  45

Phe Gly Glu Lys Gly Asp Pro Gly Ile Pro Gly Asn Pro Gly Lys Val
    50                  55                  60

Gly Pro Lys Gly Pro Met Gly Pro Lys Gly Gly Pro Gly Ala Pro Gly
65                  70                  75                  80

Ala Pro Gly Pro Lys Gly Glu Ser Gly Asp Tyr Lys Ala Thr Gln Lys
                85                  90                  95

Ile Ala Phe Ser Ala Thr Arg Thr Ile Asn Val Pro Leu Arg Arg Asp
            100                 105                 110

Gln Thr Ile Arg Phe Asp His Val Ile Thr Asn Met Asn Asn Asn Tyr
        115                 120                 125

Glu Pro Arg Ser Gly Lys Phe Thr Cys Lys Val Pro Gly Leu Tyr Tyr
    130                 135                 140

Phe Thr Tyr His Ala Ser Ser Arg Gly Asn Leu Cys Val Asn Leu Met
145                 150                 155                 160

Arg Gly Arg Glu Arg Ala Gln Lys Val Val Thr Phe Cys Asp Tyr Ala
                165                 170                 175

Tyr Asn Thr Phe Gln Val Thr Thr Gly Gly Met Val Leu Lys Leu Glu
            180                 185                 190

Gln Gly Glu Asn Val Phe Leu Gln Ala Thr Asp Lys Asn Ser Leu Leu
        195                 200                 205

Gly Met Glu Gly Ala Asn Ser Ile Phe Ser Gly Phe Leu Leu Phe Pro
    210                 215                 220

Asp Met Glu Ala
225

<210> SEQ ID NO 4
<211> LENGTH: 251
<212> TYPE: PRT

<213> ORGANISM: Homo sapiens

<400> SEQUENCE: 4

```
Met Lys Ile Pro Trp Gly Ser Ile Pro Val Leu Met Leu Leu Leu Leu
1               5                   10                  15

Leu Gly Leu Ile Asp Ile Ser Gln Ala Gln Leu Ser Cys Thr Gly Pro
            20                  25                  30

Pro Ala Ile Pro Gly Ile Pro Gly Ile Pro Gly Thr Pro Gly Pro Asp
        35                  40                  45

Gly Gln Pro Gly Thr Pro Gly Ile Lys Gly Glu Lys Gly Leu Pro Gly
    50                  55                  60

Leu Ala Gly Asp His Gly Glu Phe Gly Glu Lys Gly Asp Pro Gly Ile
65                  70                  75                  80

Pro Gly Asn Pro Gly Lys Val Gly Pro Lys Gly Pro Met Gly Pro Lys
                85                  90                  95

Gly Gly Pro Gly Ala Pro Gly Ala Pro Gly Pro Lys Gly Glu Ser Gly
            100                 105                 110

Asp Tyr Lys Ala Thr Gln Lys Ile Ala Phe Ser Ala Thr Arg Thr Ile
        115                 120                 125

Asn Val Pro Leu Arg Arg Asp Gln Thr Ile Arg Phe Asp His Val Ile
    130                 135                 140

Thr Asn Met Asn Asn Asn Tyr Glu Pro Arg Ser Gly Lys Phe Thr Cys
145                 150                 155                 160

Lys Val Pro Gly Leu Tyr Tyr Phe Thr Tyr His Ala Ser Ser Arg Gly
                165                 170                 175

Asn Leu Cys Val Asn Leu Met Arg Gly Arg Glu Arg Ala Gln Lys Val
            180                 185                 190

Val Thr Phe Cys Asp Tyr Ala Tyr Asn Thr Phe Gln Val Thr Thr Gly
        195                 200                 205

Gly Met Val Leu Lys Leu Glu Gln Gly Glu Asn Val Phe Leu Gln Ala
    210                 215                 220

Thr Asp Lys Asn Ser Leu Leu Gly Met Glu Gly Ala Asn Ser Ile Phe
225                 230                 235                 240

Ser Gly Phe Leu Leu Phe Pro Asp Met Glu Ala
                245                 250
```

<210> SEQ ID NO 5
<211> LENGTH: 217
<212> TYPE: PRT
<213> ORGANISM: Homo sapiens

<400> SEQUENCE: 5

```
Asn Thr Gly Cys Tyr Gly Ile Pro Gly Met Pro Gly Leu Pro Gly Ala
1               5                   10                  15

Pro Gly Lys Asp Gly Tyr Asp Gly Leu Pro Gly Pro Lys Gly Glu Pro
            20                  25                  30

Gly Ile Pro Ala Ile Pro Gly Ile Arg Gly Pro Lys Gly Gln Lys Gly
        35                  40                  45

Glu Pro Gly Leu Pro Gly His Pro Gly Lys Asn Gly Pro Met Gly Pro
    50                  55                  60

Pro Gly Met Pro Gly Val Pro Gly Pro Met Gly Ile Pro Gly Glu Pro
65                  70                  75                  80

Gly Glu Glu Gly Arg Tyr Lys Gln Lys Phe Gln Ser Val Phe Thr Val
                85                  90                  95

Thr Arg Gln Thr His Gln Pro Pro Ala Pro Asn Ser Leu Ile Arg Phe
```

```
            100                 105                 110
Asn Ala Val Leu Thr Asn Pro Gln Gly Asp Tyr Asp Thr Ser Thr Gly
        115                 120                 125

Lys Phe Thr Cys Lys Val Pro Gly Leu Tyr Tyr Phe Val Tyr His Ala
    130                 135                 140

Ser His Thr Ala Asn Leu Cys Val Leu Leu Tyr Arg Ser Gly Val Lys
145                 150                 155                 160

Val Val Thr Phe Cys Gly His Thr Ser Lys Thr Asn Gln Val Asn Ser
                165                 170                 175

Gly Gly Val Leu Leu Arg Leu Gln Val Gly Glu Glu Val Trp Leu Ala
            180                 185                 190

Val Asn Asp Tyr Tyr Asp Met Val Gly Ile Gln Gly Ser Asp Ser Val
        195                 200                 205

Phe Ser Gly Phe Leu Leu Phe Pro Asp
    210                 215

<210> SEQ ID NO 6
<211> LENGTH: 245
<212> TYPE: PRT
<213> ORGANISM: Homo sapiens

<400> SEQUENCE: 6

Met Asp Val Gly Pro Ser Ser Leu Pro His Leu Gly Leu Lys Leu Leu
1               5                  10                  15

Leu Leu Leu Leu Leu Ala Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
            245
```

<210> SEQ ID NO 7
<211> LENGTH: 253
<212> TYPE: PRT
<213> ORGANISM: Artificial sequence
<220> FEATURE:
<223> OTHER INFORMATION: Description of Artificial Sequence: Synthetic subunit C1qC+ additional amino acid sequence

<400> SEQUENCE: 7

```
Met Asp Val Gly Pro Ser Ser Leu Pro His Leu Gly Leu Lys Leu Leu
1               5                   10                  15

Leu Leu Leu Leu Leu Leu Ala Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp Asp Tyr Lys Asp Asp Asp Lys
                245                 250
```

<210> SEQ ID NO 8
<211> LENGTH: 8
<212> TYPE: PRT
<213> ORGANISM: Artificial sequence
<220> FEATURE:
<223> OTHER INFORMATION: Description of Artificial Sequence: Synthetic additional amino acid sequence

<400> SEQUENCE: 8

```
Asp Tyr Lys Asp Asp Asp Asp Lys
1               5
```

<210> SEQ ID NO 9
<211> LENGTH: 24
<212> TYPE: DNA
<213> ORGANISM: Artificial sequence
<220> FEATURE:

```
<223> OTHER INFORMATION: Description of Artificial Sequence: C1qA PCR
      amplification primer

<400> SEQUENCE: 9
ctagctagca tggagggtcc ccgg                                              24

<210> SEQ ID NO 10
<211> LENGTH: 22
<212> TYPE: DNA
<213> ORGANISM: Artificial sequence
<220> FEATURE:
<223> OTHER INFORMATION: Description of Artificial Sequence: C1qA PCR
      amplification primer

<400> SEQUENCE: 10
ccggaattct caggcagatg gg                                                22

<210> SEQ ID NO 11
<211> LENGTH: 24
<212> TYPE: DNA
<213> ORGANISM: Artificial sequence
<220> FEATURE:
<223> OTHER INFORMATION: Description of Artificial Sequence: C1qB PCR
      amplification primer

<400> SEQUENCE: 11
ctagctagca tgaagatccc atgg                                              24

<210> SEQ ID NO 12
<211> LENGTH: 21
<212> TYPE: DNA
<213> ORGANISM: Artificial sequence
<220> FEATURE:
<223> OTHER INFORMATION: Description of Artificial Sequence: C1qB PCR
      amplification primer

<400> SEQUENCE: 12
cgcggatcct caggcctcca t                                                 21

<210> SEQ ID NO 13
<211> LENGTH: 24
<212> TYPE: DNA
<213> ORGANISM: Artificial sequence
<220> FEATURE:
<223> OTHER INFORMATION: Description of Artificial Sequence: C1qC PCR
      amplification primer

<400> SEQUENCE: 13
ctagctagca tggacgtggg gccc                                              24

<210> SEQ ID NO 14
<211> LENGTH: 25
<212> TYPE: DNA
<213> ORGANISM: Artificial sequence
<220> FEATURE:
<223> OTHER INFORMATION: Description of Artificial Sequence: C1qC PCR
      amplification primer

<400> SEQUENCE: 14
ccggaattcc tagtcgggga agagc                                             25

<210> SEQ ID NO 15
<211> LENGTH: 65
<212> TYPE: DNA
<213> ORGANISM: Artificial sequence
<220> FEATURE:
<223> OTHER INFORMATION: Description of Artificial Sequence: PCR primer
``` for site-directed mutagenesis of C1qC

<400> SEQUENCE: 15
ggcttcctgc tcttccccga cgattacaag gatgacgacg ataagtagga gttctgcaga    60
tatcc                                                                65

<210> SEQ ID NO 16
<211> LENGTH: 65
<212> TYPE: DNA
<213> ORGANISM: Artificial sequence
<220> FEATURE:
<223> OTHER INFORMATION: Description of Artificial Sequence: PCR primer
      for site-directed mutagenesis of C1qC

<400> SEQUENCE: 16
ggatatctgc agaactccta cttatcgtcg tcatccttgt aatcgtcggg gaagagcagg    60
aagcc                                                                65

<210> SEQ ID NO 17
<211> LENGTH: 10
<212> TYPE: PRT
<213> ORGANISM: Artificial sequence
<220> FEATURE:
<223> OTHER INFORMATION: Description of Artificial Sequence: Synthetic
      additional amino acid sequence

<400> SEQUENCE: 17

Glu Gln Lys Leu Ile Ser Glu Glu Asp Leu
1               5                   10

<210> SEQ ID NO 18
<211> LENGTH: 60
<212> TYPE: DNA
<213> ORGANISM: Artificial sequence
<220> FEATURE:
<223> OTHER INFORMATION: Description of Artificial Sequence: C1qC PCR
      amplification primer

<400> SEQUENCE: 18
cccctcaggg gccaagccga ttacaaggat gacgacgata agaacacagg ctgctacggg    60

<210> SEQ ID NO 19
<211> LENGTH: 60
<212> TYPE: DNA
<213> ORGANISM: Artificial sequence
<220> FEATURE:
<223> OTHER INFORMATION: Description of Artificial Sequence: C1qC PCR
      amplification primer

<400> SEQUENCE: 19
cccgtagcag cctgtgttct tatcgtcgtc atccttgtaa tcggcttggc ccctgagggg    60

<210> SEQ ID NO 20
<211> LENGTH: 6
<212> TYPE: PRT
<213> ORGANISM: Artificial sequence
<220> FEATURE:
<223> OTHER INFORMATION: Description of Artificial Sequence: Synthetic
      6-Histidine tag

<400> SEQUENCE: 20

His His His His His His
1               5

<210> SEQ ID NO 21

-continued

```
<211> LENGTH: 51
<212> TYPE: DNA
<213> ORGANISM: Artificial sequence
<220> FEATURE:
<223> OTHER INFORMATION: Description of Artificial Sequence: C1qC PCR
      amplification primer

<400> SEQUENCE: 21
gctcttcccc gaccatcacc atcaccatca ctaggagttc tgcagatatc c          51

<210> SEQ ID NO 22
<211> LENGTH: 51
<212> TYPE: DNA
<213> ORGANISM: Artificial sequence
<220> FEATURE:
<223> OTHER INFORMATION: Description of Artificial Sequence: C1qC PCR
      amplification primer

<400> SEQUENCE: 22
ggatatctgc agaactccta gtgatggtga tggtgatggt cggggaagag c          51

<210> SEQ ID NO 23
<211> LENGTH: 253
<212> TYPE: PRT
<213> ORGANISM: Artificial sequence
<220> FEATURE:
<223> OTHER INFORMATION: Description of Artificial Sequence: Synthetic
      subunit C1qC+ additional amino acid sequence in N-terminal
      position

<400> SEQUENCE: 23

Met Asp Val Gly Pro Ser Ser Leu Pro His Leu Gly Leu Lys Leu Leu
1               5                   10                  15

Leu Leu Leu Leu Leu Leu Ala Leu Arg Gly Gln Ala Asp Tyr Lys Asp
            20                  25                  30

Asp Asp Asp Lys Asn Thr Gly Cys Tyr Gly Ile Pro Gly Met Pro Gly
        35                  40                  45

Leu Pro Gly Ala Pro Gly Lys Asp Gly Tyr Asp Gly Leu Pro Gly Pro
    50                  55                  60

Lys Gly Glu Pro Gly Ile Pro Ala Ile Pro Gly Ile Arg Gly Pro Lys
65                  70                  75                  80

Gly Gln Lys Gly Glu Pro Gly Leu Pro Gly His Pro Gly Lys Asn Gly
                85                  90                  95

Pro Met Gly Pro Pro Gly Met Pro Gly Val Pro Gly Pro Met Gly Ile
            100                 105                 110

Pro Gly Glu Pro Gly Glu Glu Gly Arg Tyr Lys Gln Lys Phe Gln Ser
        115                 120                 125

Val Phe Thr Val Thr Arg Gln Thr His Gln Pro Pro Ala Pro Asn Ser
    130                 135                 140

Leu Ile Arg Phe Asn Ala Val Leu Thr Asn Pro Gln Gly Asp Tyr Asp
145                 150                 155                 160

Thr Ser Thr Gly Lys Phe Thr Cys Lys Val Pro Gly Leu Tyr Tyr Phe
                165                 170                 175

Val Tyr His Ala Ser His Thr Ala Asn Leu Cys Val Leu Leu Tyr Arg
            180                 185                 190

Ser Gly Val Lys Val Val Thr Phe Cys Gly His Thr Ser Lys Thr Asn
        195                 200                 205

Gln Val Asn Ser Gly Gly Val Leu Leu Arg Leu Gln Val Gly Glu Glu
    210                 215                 220

Val Trp Leu Ala Val Asn Asp Tyr Tyr Asp Met Val Gly Ile Gln Gly
```

```
225                 230                 235                 240
Ser Asp Ser Val Phe Ser Gly Phe Leu Leu Phe Pro Asp
                245                 250

<210> SEQ ID NO 24
<211> LENGTH: 251
<212> TYPE: PRT
<213> ORGANISM: Artificial sequence
<220> FEATURE:
<223> OTHER INFORMATION: Description of Artificial Sequence: Synthetic
      subunit C1qC+6His

<400> SEQUENCE: 24

Met Asp Val Gly Pro Ser Ser Leu Pro His Leu Gly Leu Lys Leu Leu
1               5                   10                  15

Leu Leu Leu Leu Leu Leu Ala Leu Arg Gly Gln Ala Asn Thr Gly Cys
                20                  25                  30

Tyr Gly Ile Pro Gly Met Pro Gly Leu Pro Gly Ala Pro Gly Lys Asp
            35                  40                  45

Gly Tyr Asp Gly Leu Pro Gly Pro Lys Gly Glu Pro Gly Ile Pro Ala
        50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp His His His His His His
                245                 250
```

METHOD FOR PREPARING C1Q RECOMBINANT PROTEIN

SEQUENCE LISTING

The instant application contains a Sequence Listing which has been filed electronically in ASCII format and is hereby incorporated by reference in its entirety. Said ASCII copy, created on Jul. 21, 2015, is named F0263500529-US-PCT_SL.txt and is 23,473 bytes in size.

SUBJECT OF THE INVENTION

The present invention relates to a method for preparing the C1q protein recombinantly.

TECHNICAL BACKGROUND

The C1q protein belongs to the C1 complex which initiates the conventional pathway of activation of the complement system which participates in innate immunity in mammals. In addition to C1q, the initiating complex comprises two serine proteases, C1r and C1s, associated as a C1s-C1r-C1r-C1s tetramer. The binding of C1q to "danger signals", namely antigen-antibody complexes, in particular of the IgG type, and factors present at the surface of pathogenic agents, of infected cells or of apoptotic cells, results in the autoactivation of C1r, which activates C1s. Activated C1s then initiates the activation in cascade of the other complement components.

By virtue of its central role in the conventional complement activation pathway, a deficiency in C1q increases the sensitivity of the affected individual to microbial infections, such as *Salmonella* infections, malarial reinfection and polymicrobial peritonitis, but also causes excessive inflammation and autoimmunity of the lupus type, thereby indicating a tolerogenic or immunosuppressor role for C1q (Lu J. et al. (2008) *Cellular & Molecular Immunology* 5:9-21). As regards the latter disease, it has, moreover, been shown that patients suffering from systemic lupus erythematosus can be treated using an extracorporeal blood circulation system including a step of passing the blood over a C1q protein-based immunoadsorption column (Pfueller B. et al. (2001) *Arthritis & Rheumatism* 44:1962-1963).

Thus, it would be advantageous, in particular in a therapeutic or diagnostic context, or more broadly a scientific research context, to have safe and reproducible sources of C1q protein.

However, the structure of C1q makes complex the production thereof by synthesis. Indeed, C1q is a multimeric protein of high molecular weight (approximately 460 kDa) consisting of the association of 18 polypeptide chains: 6 C1qA subunits, 6 C1qB subunits and 6 C1qC subunits. Each subunit, or chain, contains a collagen-type N-terminal domain and a globular C-terminal domain. The C1qA subunit is associated with a C1qB subunit via the formation of a disulfide bridge and with a C1qC subunit noncovalently so as to form a heterotrimer. Moreover, the C1qC subunits are each connected in pairs via the formation of a disulfide bridge. For each heterotrimer, the collagen-type domains associate to form a triple helix which is also of collagen type, and the globular domains associate to form a virtually spherical globular region (Gaboriaud C. et al. (2003) *Journal of Biological Chemistry* 278:46974-46982). The overall shape of C1q is therefore that of a "bouquet of tulips" where the six globular regions emerge from a tail made up of the six collagen-type triple helices (FIG. 1).

Consequently, at the current time, the only means of obtaining complete C1q protein is to extract it from human or animal serum, which is satisfactory neither in terms of reproducibility, nor in terms of biological safety, since blood derivatives may be contaminated with viruses, prions or else single-cell parasites. As regards the recombinant route, which would make it possible to solve these problems, it has been possible to produce only subunits or fragments, in particular globular ones (see, for example, Kojouharova M. et al. (2004) *Journal of Immunology* 172:4351-4358), of C1q.

It is therefore an object of the invention to provide a reproducible method for obtaining complete and correctly structured C1q protein without associated biological risk.

DESCRIPTION OF THE INVENTION

The present invention ensues from the unexpected demonstration, by the inventors, that the addition of a peptide of sequence DYKDDDDK (SEQ ID No. 8) to the C-terminal end of the C1qC subunit makes it possible, when it is produced recombinantly with the C1qA and C1qB subunits in the same cell during an in vitro cell culture, to generate a C1q protein having a structure similar to its native structure.

Thus, the present invention relates to a method for producing a C1q protein, or a C1q protein variant, recombinantly, in which the protein is recovered from an in vitro culture of cells expressing a C1qA subunit or a C1qA subunit variant, a C1qB subunit or a C1qB subunit variant, and a C1qC subunit or a C1qC subunit variant, and in which at least one of the subunits, or at least one of the subunit variants, also bears, at the N-terminal or C-terminal end, an additional amino acid sequence of at least 6 residues, at least 40% of which are glutamic acid and/or aspartic acid residues.

The present invention also relates to a C1q protein, or a C1q protein variant, comprising a C1qA subunit or a C1qA subunit variant, a C1qB subunit or a C1qB subunit variant, and a C1qC subunit or a C1qC subunit variant, and in which at least one of the subunits, or at least one of the subunit variants, also bears, at the N-terminal or C-terminal end, an additional amino acid sequence of at least 6 residues, at least 40% of which are glutamic acid and/or aspartic acid residues.

The present invention also relates to a C1q protein subunit or subunit variant bearing, at the N-terminal or C-terminal end, an additional amino acid sequence of at least 6 residues, at least 40% of which are glutamic acid and/or aspartic acid residues.

The present invention also relates to a nucleic acid encoding a C1q protein subunit or subunit variant according to the invention.

The present invention also relates to a vector comprising a nucleic acid according to the invention.

The present invention also relates to a cell comprising a nucleic acid or a vector according to the invention. In one preferred embodiment of the cell according to the invention, it also comprises one or more nucleic acids or one or more vectors encoding the complementary subunits or subunit variants of C1q, such that the cell comprises one or more nucleic acids or vectors encoding a C1qA subunit or a C1qA subunit variant, a C1qB subunit or a C1qB subunit variant, and a C1qC subunit or a C1qC subunit variant, and in which at least one of the subunits, or of the subunit variants, also bears, at the N-terminal or C-terminal end, an additional amino acid sequence of at least 6 residues, at least 40% of which are glutamic acid and/or aspartic acid residues.

The present invention also relates to the use of a nucleic acid or of a vector according to the invention, for the transformation of a cell and the production of C1q by the cell.

The C1q protein belonging to the C1 complex of the complement system is well known to those skilled in the art. It is in particular described in Gaboriaud C. et al. (2003) *Journal of Biological Chemistry* 278:46974-46982. As intended herein, the C1q protein denotes a complete protein, i.e. a protein consisting of the association of 18 subunits, namely 6 C1qA subunits (or chains), 6 C1qB subunits (or chains) and 6 C1qC subunits (or chains). Preferably, the C1q protein according to the invention is human. By way of example, the sequence of the C1qA subunit is preferably represented by SEQ ID No. 1, the sequence of the C1qB subunit is preferably represented by SEQ ID No. 3 and the sequence of the C1qC subunit is preferably represented by SEQ ID No. 5.

As intended herein, a subunit "variant" derives from the subunit by the insertion, the deletion or the substitution of at least one amino acid, with the proviso that the sequence of the variant has at least 70%, preferably at least 80%, more preferably at least 90% and even more preferably at least 95% identity with the sequence of the subunit from which it derives and that the subunit variant makes it possible to form a variant of C1q.

As intended herein, the percentage identity between two peptide sequences can be determined by producing an optimal alignment over the entire length of the sequences, by determining the number of aligned positions for which the amino acids are identical in each sequence and by dividing this number by the total number of amino acids in the longer of the two sequences. The optimal alignment is that which gives the highest percentage identity between the two sequences. Moreover, spaces or gaps, generally corresponding to amino acids gained or lost by either of the sequences during evolution, can be introduced into either of the sequences, to an extent that those skilled in the art know how to access, in order to produce an optimal alignment. Those skilled in the art have, moreover, at their disposal numerous algorithms or pieces of software capable of producing an automated optimal alignment between two peptide sequences. By way of example, mention will in particular be made of the algorithm of Needleman & Wunsch (1970) *J. Mol. Biol.* 48:443-453, which can in particular be implemented by means of the EMBOSS Needle software with the following default parameters:

Matrix: Blosum62;
Gap open: 10;
Gap extend: 0.5;
Output format: pair;
End gap penalty: false;
End gap open: 10;
End gap extend: 0.5.

As intended herein, a C1q variant consists of the association of 6 C1qA subunits or C1qA subunit variants, of 6 C1qB subunits or C1qB subunit variants, and of 6 C1qC subunits or C1qC subunit variants and contains at least one subunit variant. Preferably, the C1q variant according to the invention does not consist of the association of subunits of which all the globular domains or all the collagen-type domains are missing.

Preferably, the C1q protein, or the C1q protein variant, according to the invention or produced according to the invention is such that the C1qA subunits, or the C1qA subunit variants, are connected to the C1qB subunits, or to the C1qB subunit variants, via a disulfide bridge. Likewise preferably, the C1q protein, or the C1q protein variant, according to the invention or produced according to the invention, is such that the C1qC subunits are connected in pairs via a disulfide bridge. Likewise preferably, the C1q protein, or the C1q protein variant, according to the invention or produced according to the invention, has a structure, which is in particular visible by electromicroscopy, in the form of a bouquet of tulips. Likewise preferably, the C1q protein, or the C1q protein variant, according to the invention or produced according to the invention, has a dissociation constant ($K_D$) with respect to the C1s-C1r-C1r-C1s tetramer which is equal at ±20% to that of the C1q protein isolated from serum, in particular human serum, measured under the same conditions. Likewise preferably, the C1q protein, or the C1q protein variant, according to the invention or produced according to the invention, has a dissociation constant ($K_D$) with respect to immunoglobulins, in particular of G type, which is equal at ±20% to that of the C1q protein isolated from serum, in particular human serum, measured under the same conditions. As intended herein, the C1q protein isolated from serum is in particular purified by applying the method described by Arlaud G J et al. (1979) *Mol. Immunol.* 16:445-450 and presented in part 4a) of the example. Likewise preferably, the C1q protein or the C1q protein variant, according to the invention or produced according to the invention, makes it possible, when it is associated with the C1s-C1r-C1r-C1s tetramer, to cause C1s activation. Finally, preferably, the C1q protein, or the C1q protein variant, produced according to the invention can bind to an ovalbumin-anti-ovalbumin antibody immune complex. The ovalbumin-anti-ovalbumin antibody immune complex is in particular described in Arlaud G J et al. (1979) *Mol. Immunol.* 16:445-450.

As intended herein, the recombinant production means that the C1q protein or the C1q variant according to the invention is produced by cells which express at least one subunit encoded by a nucleic acid or a vector which has been introduced, in particular by transformation or transfection, into the cell. Preferably, nucleic acids or vectors encoding:

a C1qA subunit or a C1qA subunit variant, and
a C1qB subunit or a C1qB subunit variant, and
a C1qC subunit or a C1qC subunit variant, and of which at least one of the subunits, or at least one of the subunit variants, also bears, at the N-terminal or C-terminal end, an additional amino acid sequence of at least 6 residues, at least 40% of which are glutamic acid and/or aspartic acid residues, have been introduced into the cells according to the invention. In this case, one, two or the three sequences encoding respectively a C1qA subunit or a C1qA subunit variant, a C1qB subunit or a C1qB subunit variant, and a C1qC subunit or a C1qC subunit variant may be present in a nucleic acid or a vector according to the invention.

However, it is preferred that each sequence encoding respectively a C1qA subunit or a C1qA subunit variant, a C1qB subunit or a C1qB subunit variant, and a C1qC subunit or a C1qC subunit variant be present on its own nucleic acid or vector. The three nucleic acids or vectors may then be introduced concomitantly or sequentially into the cell according to the invention. When the introduction is sequential, a first nucleic acid or vector is introduced, then a second nucleic acid or vector is introduced, optionally after obtaining a cell line stably expressing the subunit or the subunit variant encoded by the first nucleic acid or vector, then a third nucleic acid or vector is introduced, optionally after obtaining a cell line stably expressing, in addition, the subunit or the subunit variant encoded by the second nucleic acid or vector. When the introduction is concomitant, (i) the three nucleic acids or vectors may be introduced at the same time, or (ii) a first nucleic acid or vector is introduced and then the second and third nucleic acids or vectors are introduced at the same time, optionally after obtaining a cell line stably expressing the subunit or the subunit variant encoded by the first nucleic acid or vector, or (iii) a first nucleic acid or vector and a second nucleic acid or vector are introduced at the same time and then a third nucleic acid or vector is introduced, optionally after obtaining a cell line stably expressing the subunits or the subunit variants encoded by the first and second nucleic acids or vectors.

As intended herein, the expression "in vitro culture" means that the cells producing the C1q protein, or a C1q protein variant according to the invention, are cultured outside a living organism.

Moreover, in the in vitro culture according to the invention, the same cell produces at the same time:
   a C1qA subunit or a C1qA subunit variant, and
   a C1qB subunit or a C1qB subunit variant, and
   a C1qC subunit or a C1qC subunit variant.

The vector according to the invention may be of any type. However, it is preferably a eukaryotic, in particular mammalian, expression vector therefore comprising all the elements required for maintaining it and for the expression of the nucleic acid according to the invention in a cell according to the invention. The vector according to the invention is thus preferably in particular a plasmid comprising a eukaryotic promoter and a eukaryotic terminator, a eukaryotic origin of replication, and a eukaryotic selection gene, and also preferably a prokaryotic origin of replication and a prokaryotic selection gene, such as a plasmid of the pcDNA3.1 type for example.

The cells according to the invention may be of any type. However, they are preferably eukaryotic cells, in particular mammalian cells and more particularly human cells. Preferably, the cells according to the invention are cell line cells, i.e. cells having an essentially unlimited cell division potential. Particularly preferably, the cells according to the invention are chosen from the group consisting of 293-F, HEK-293, CHO, COS-7, BHK-21, NSO and SP2/0 cells.

Preferably, the cells according to the invention stably express the C1qA subunit or the C1qA subunit variant, the C1qB subunit or the C1qB subunit variant, and the C1qC subunit or the C1qC subunit variant. As intended herein, a stable expression means that the potentiality of expression of the subunits, or of the subunit variants, by the cell does not disappear as long as the cell retains the general potentiality of expressing proteins and/or as long as the nucleic acids encoding the subunits or the subunit variants are integrated into the chromosomes of the cell.

Preferably, the additional amino acid sequence according to the invention comprises at least 7 or 8 amino acids. Likewise preferably, the additional amino acid sequence according to the invention comprises at most 20, 15, 10 or 8 amino acids. Likewise preferably, the additional amino acid sequence according to the invention comprises at least 50%, more preferably at least 55% and even more preferably at least 60% of aspartic acid and/or glutamic acid amino acids. Likewise preferably, the additional amino acid sequence according to the invention comprises at least 50%, more preferably at least 55% and even more preferably at least 60% of aspartic acid amino acids. In the context of the present description, aspartic acid may also be referred to as aspartate, Asp or D, and glutamic acid may also be referred to as glutamate, Glu, or E. Likewise preferably, the additional amino acid sequence according to the invention does not comprise a sequence encoding a Myc tag. Particularly preferably, the amino acid sequence is the following: DYKDDDDK (SEQ ID No. 8) or EQKLISEEDL (SEQ ID No. 17).

The additional amino acid sequence according to the invention may be placed without distinction on the N-terminal side or on the C-terminal side of the subunits or of the subunit variants according to the invention; however, it is preferably located at the C-terminal end of at least one of the subunits or of the subunit variants. Preferably, the additional amino acid sequence according to the invention is located at the N-terminal or C-terminal end, preferably at the C-terminal end, of the C1qC subunit or of a C1qC subunit variant according to the invention. Likewise, the additional amino acid sequence according to the invention is preferably directly attached to the C-terminal or N-terminal end of the subunits or of the subunit variants according to the invention, that is to say there is no intermediate sequence or sequence between the additional sequence and sequence of the subunits or of the subunit variants according to the invention. Very particularly preferably, the additional amino acid sequence according to the invention is directly attached to the C-terminal end of the C1qC subunit or of a C1qC subunit variant according to the invention and, in this case, the sequence of the C1qC subunit bearing the additional amino acid sequence according to the invention is preferably represented by SEQ ID No. 7. Moreover, preferably, the additional amino acid sequence according to the invention is cleavable, that is to say it can be removed, entirely or partly, from the C1q protein after production thereof according to the invention. In particular, when it is cleavable, the additional amino acid sequence according to the invention contains a cleavage site for a protease. As those skilled in the art will clearly understand, a part of the constituent amino acids of the protease recognition site may be on the portion of the subunit or of the subunit variant adjoining the additional amino acid sequence according to the invention. Moreover, by way of example of a protease, mention may be made of enterokinase which causes a cleavage after the lysine (K) of the DDDK cleavage site.

The C1q protein, or the C1q protein variant, can be easily recovered from the culture according to the invention, and then can optionally be purified, using numerous techniques well known to those skilled in the art. Preferably, the C1q protein, or the C1q protein variant, is recovered from the culture supernatant according to the invention, that is to say the non-cellular part of the culture, more preferably as is indicated in the examples which follow.

Preferably, the in vitro culture according to the invention contains vitamin C, in particular at a concentration of 20 to 200 μg/ml, more preferably at a concentration of 80 to 120 μg/ml and even more preferably at a concentration of about 100 μg/ml.

The invention will be explained further, in a nonlimiting manner, by means of the figures and the example which follows.

EXAMPLES

Example 1

Figure 1:
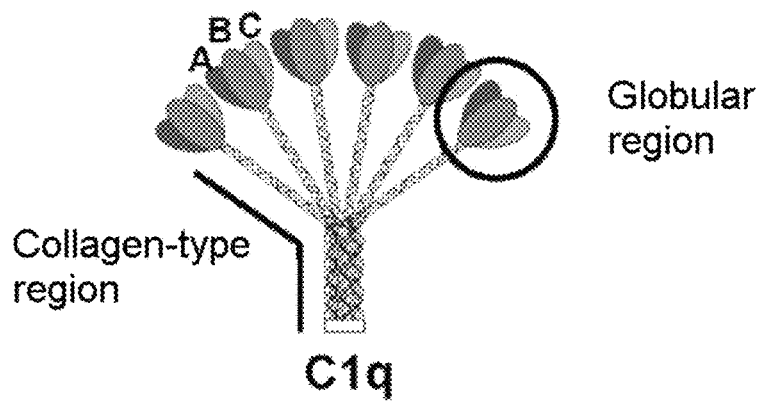
FIG. 1 represents the quaternary structure, termed "bouquet of tulips" structure, of the C1q protein, resulting from the association of 6 C1qA subunits, 6 C1qB subunits and 6 C1qC subunits, and distinguishing the globular and collagen-type regions.

1. Cloning of Recombinant C1q
a) Inserts Preparation
Clones harboring the sequences encoding the C1qA, C1qB and C1qC subunits, respectively defined by the GenBank database identifiers NM 015991, NM 000491 and NM 172369, were obtained from Origene (Rockville, Md., USA) (see Table 1).

TABLE 1

| ORIGENE clones |
| --- |
| C1qA-pcMV6-Ac (NM 015991) |
| C1qB-pc MV6-XL4 (NM 000491) |
| C1qC-pc MV6-XL4 (NM 172369) |

The C1qA, C1qB and C1qC clones were amplified by transformation with 5 ng of DNA in *Escherichia coli* DH5a bacteria (Invitrogen) and then purified using the QIAPrep Miniprep kit from Qiagen.

The coding sequences of the C1qA, C1qB and C1qC subunits were then amplified using the primer oligonucleotides presented in Table 2 using the following protocol:
Reaction mixture:
Template (clone): 200 ng
$MgSO_4$: 2 mM
dNTPs: 400 µM
Primers: 100 pmol
Vent polymerase (New England Biolabs): 2 U
PCR cycles:

| 1. | 95° C. | 2 min |
| --- | --- | --- |
| 2. | 95° C. | 1 min |
| 3. | 60° C. | 1 min |
| 4. | 72° C. | 1 min |
| Cycles 2 to 4 are repeated 35 times | | |
| 5. | 72° C. | 5 min |

TABLE 2

| Chain | Upstream primer (5'-3') | Downstream primer (5'-3') |
| --- | --- | --- |
| C1qA | CTAGCTAGCATGGA GGGTCCCCGG (SEQ ID No. 9) | CCGGAATTCTCAGGC AGATGGG (SEQ ID No. 10) |
| C1qB | CTAGCTAGCATGAA GATCCCATGG (SEQ ID No. 11) | CGCGGATCCTCAGGC CTCCAT (SEQ ID No. 12) |
| C1qC | CTAGCTAGCATGGA CGTGGGGCCC (SEQ ID No. 13) | CCGGAATTCCTAGTC GGGGAAGAGC (SEQ ID No. 14) |

The PCR amplification products are then purified using the QIAquick PCR purification kit (Qiagen) and then cleaved using the NheI and EcoRI restriction enzymes for C1qA and C1qC, and the NheI and BamHI restriction enzymes for C1qB. The cleaved fragments are finally purified again using the QIAquick PCR purification kit.

b) Vectors Preparation
pcDNA3.1. vectors (Invitrogen) incorporating respectively 3 distinct antibiotic resistance genes (see Table 3) were used to receive the inserts.
The vectors are cleaved with the following enzymes (see also Table 3):
NheI and EcoRI for pcDNA3.1 and pcDNA3.1/zeomycin
NheI and BamHI for pcDNA3.1/hygromycin
The cleaved vectors were subjected to conventional dephosphorylation using the Shrimp alkaline phosphatase kit (Roche) and were then purified using the QIAquick DNA purification kit (Qiagen).

TABLE 3

| (Neomycin = G418 = Geneticin) | | |
| --- | --- | --- |
| Subunit | Cleavage sites | Expression vectors (resistance gene) |
| C1qA | NheI-EcoRI | pcDNA3.1 (neomycin) |
| C1qB | NheI-BamHI | pcDNA3.1 (hygromycin) |
| C1qC | NheI-EcoRI | pcDNA3.1 (zeocin) | c) Cloning
The Rapid DNA ligation kit (Roche) was used to ligate the inserts into the cleaved vectors. The vector and the insert were mixed in a vector/insert molar ratio=1/5, i.e. 50 ng of vector (approximately 5300 bp) for 35 ng of insert (approximately 700 bp). The ligation mixture is incubated for 30 minutes at ambient temperature and E. coli DH5a bacteria are transformed with 2.5 µl of the mixture. The DNA of the transformed bacteria resistant to the appropriate antibiotic is extracted and then screened by means of the restriction enzymes used for the cloning. The plasma DNA of the selected bacteria is then sequenced.

d) C-terminal Insertion of the DYKDDDDK Sequence (SEQ ID No. 8)

The DYKDDDDK sequence (SEQ ID No. 8) was inserted at the C-terminal end of the C1qC subunit by site-directed mutagenesis using the Quickchange kit (Agilent) so as to form the C1qC subunit+peptide.

Briefly, the pcDNA3.1.C1qC plasmid is amplified by PCR using two complementary primers incorporating the sequence encoding the peptide to be inserted and binding respectively to the two strands of the plasmid. For this, a reaction mixture comprising 200 ng of the pcDNA3.1.C1qC plasmid and 225 ng of an oligonucleotide having the sequence GGCTTCCTGCTCTTCCCCGAC GATTACAAGGATGACGACGATAAGTAGGAGTTCT GCAGATATCC (SEQ ID No. 15) and of an oligonucleotide having the sequence GGATATCTGCAGAACTCCTA CTTATCGTCGTCATCCTTGTAATCGTCGGGGAAGA GCAGGAAGCC (SEQ ID No. 16) is prepared (the parts underlined correspond to the sequence of the peptide to be inserted). 5 µl of "Quick solution", 1 µl of "dNTP mix" and 1 µl of Pfu Turbo DNA polymerase (2.5 U/µl) (Agilent) are added to the mixture before amplification.

The amplification is then carried out under the following conditions:

| Cycle 1 | 95° C. | 1 min |
| Cycle 2 | 95° C. | 50 sec |
| Cycle 3 | 60° C. | 50 sec |
| Cycle 4 | 68° C. | 12 min |
| Cycles 2 to 4 are repeated 18 times | | |
| Cycle 5 | 68° C. | 7 min |

Two consecutive treatments of 1 hour with 1 µl of DpnI nuclease (10 U/µl) are then carried out in order to destroy the pcDNA3.1.C1qC template plasmids, then 2 µl of the mixture are used to transform E. coli XL10 Gold bacteria (Agilent).

The DNA of the transformed bacteria resistant to zeocin is extracted and then screened using the EcoRI restriction enzyme. The plasmid DNA of the selected bacteria is then sequenced.

The sequences of the three C1q chains obtained are represented hereinafter:

C1qA
(SEQ ID No. 2)
MEGPRGWLVLCVLAISLASMVTEDLCRAPDGKKGEAGRPGRRGRPGLKGE

QGEPGAPGIRTGIQGLKGDQGEPGPSGNPGKVGYPGPSGPLGARGIPGIK

GTKGSPGNIKDQPRPAFSAIRRNPPMGGNVVIFDTVITNQEEPYQNHSGR

FVCTVPGYYYFTFQVLSQWEICLSIVSSSRGQVRRSLGFCDTTNKGLFQV

VSGGMVLQLQQGDQVWVEKDPKKGHIYQGSEADSVFSGFLIFPSA

C1qB
(SEQ ID No. 4)
MKIPWGSIPVLMLLLLLGLIDISQAQLSCTGPPAIPGIPGIPGTPGPDGQ

PGTPGIKGEKGLPGLAGDHGEFGEKGDPGIPGNPGKVGPKGPMGPKGGPG

-continued
APGAPGPKGESGDYKATQKIAFSATRTINVPLRRDQTIRFDHVITNMNNN

YEPRSGKFTCKVPGLYYFTYHASSRGNLCVNLMRGRERAQKVVTFCDYAY

NTFQVTTGGMVLKLEQGENVFLQATDKNSLLGMEGANSIFSGFLLFPDME

A

C1qC + peptide
(SEQ ID No. 7)
MDVGPSSLPHLGLKLLLLLLLLALRGQANTGCYGIPGMPGLPGAPGKDGY

DGLPGPKGEPGIPAIPGIRGPKGQKGEPGLPGHPGKNGPMGPPGMPGVPG

PMGIPGEPGEEGRYKQKFQSVFTVTRQTHQPPAPNSLIRFNAVLTNPQGD

YDTSTGKFTCKVPGLYYFVYHASHTANLCVLLYRSGVKVVTFCGHTSKTN

QVNSGGVLLRLQVGEEVWLAVNDYYDMVGIQGSDSVFSGFLLFPDDYKDD

DDK

The sequence of the peptide is underlined and the sequences of the mature chains (after cleavage of the signal peptide) are indicated in bold.

2. Stable Transfections of 293 F Cells a) Generation of Stable Lines Producing 1 Chain (C1qA, C1qB or C1qC+Peptide)

293-F cells (Invitrogen) in suspension, cultured in serum-free FreeStyle 293 expression medium (Invitrogen), were used.

Transfection

The following mixture was prepared on day D:

$30 \times 10^6$ 293-F cells in suspension in 30 ml of serum FreeStyle 293 expression medium (Invitrogen).

30 µg of DNA in Optimem medium (Invitrogen) (pcDNA3.1 containing the DNA encoding the chain of interest).

60 µl of 293-Fectin (Invitrogen) in Optimem medium (Invitrogen).

Cells in 293F medium and (DNA+transfectant).

Establishment of Stable Lines

D+3: change of medium (sample taken in order to verify protein production by electrophoresis and Western blot) with addition:

of the appropriate selection antibiotic:

G418 (neomycin) 400 µg/ml final concentration (C1qA)

hygromycin 100 µg/ml final concentration (C1qB)

zeocin 10 µg/ml final concentration (C1qC or C1qC+peptide)

of vitamin C 100 µg/ml final concentration (for correct folding of the collagen-type helices).

The culture was maintained with passage twice a week (volume adjusted according to the number of living cells so as to remain between 1 and $1.2 \times 10^6$ living cells/ml) until the resistant cells begin to multiply (generally at D+21).

At D+38: verification of protein production by gel electrophoresis and labeling of a Western blot with anti-C1qA chain, anti-C1qB chain, anti-C1qC chain or anti-peptide antibodies.

At D+40: the cells are frozen.

b) Generation of Stable Lines Producing 2 C1q Chains

This protocol was used to straightaway generate a line producing the C1qA+C1qB chains, but it can be applied for C1qA+C1qC and C1qB+C1qC. The transfection was carried out as indicated above by bringing $30 \times 10^6$ cells into contact with 30 µg of total DNA (15 µg of plasmid DNA encoding each of the two chains). The selection of stable transfectants was carried out with the appropriate pair of antibiotics (each at the same concentration as if it was used alone).

Alternatively, it is possible to transfect a stable line already producing a chain with the DNA encoding a second chain under the same conditions (sequential transfection). The latter protocol was used to generate stable lines producing C1qA and C1qC+peptide and also C1qB and C1qC+peptide.

c) Generation of Stable Lines Producing the 3 C1q Chains

The same protocol as indicated above was used to transfect a stable line already producing two chains with the DNA encoding the third chain, and to select the stable transfectants in the presence of the three antibiotics.

Alternatively, it is possible to transfect a stable line producing one chain with the DNA encoding the other two chains (30 µg of total DNA containing 15 µg encoding each of the two chains), the selection being carried out in the presence of the three antibiotics.

The verification of the presence of the three chains is carried out by labeling with a Western blot with anti-C1qA chain, anti-C1qB chain, anti-C1qC chain and anti-peptide antibodies.

The inventors thus produced the following stable lines:
C1qA (A)
C1qB (B)
C1qC+peptide (C)
C1qAB (AB) (concomitant transfection with pcDNA3.1.C1qA and pcDNA3.1.C1qB)
C1qC+peptide+C1qA (C+A)
C1qC+peptide+C1qB (C+B)
C1qAB+C1qC+peptide (AB+C) (concomitant transfection with pcDNA3.1.C1qA and pcDNA3.1.C1qB in a first step, then with C1qC+peptide in a second step)
C1qC+peptide+C1qA+C1q B (C+A+B)
C1qC+peptide+C1qB+C1qA (C+B+A)

3. Recombinant Protein Production

The C1qAB+C1qC+peptide stable line was cultured in the serum-free FreeStyle 293 expression medium (Invitrogen).

Starting from D+10, samples of the supernatant were taken every 72 h for 2 to 3 weeks.

4. Purification

A two-step purification was carried out. In a first step, a purification of the culture supernatant using ovalbumin-antiovalbumin immune complexes was carried out in a manner similar to what has been previously described for the purification of C1q from human serum by Arlaud G J et al. (1979) *Mol. Immunol.* 16:445-450. Then, in a second step, a purification by affinity chromatography was carried out.

a) Adsorption of the Culture Supernatant onto Immune Complexes

Step 1: Immune Complex Conditioning (Stock Solution at 10 mg/ml)
centrifugation for 8 min at 9000 rpm (4° C.) and pellet taken out with 20 mM Tris buffer, 120 mM NaCl, 2.5 mM $CaCl_2$, pH 7.4;
incubation for 30 min at 30° C. with 2 mM DFP (protease inhibitor); then
washing with 20 mM Tris buffer, 120 mM NaCl, 2.5 mM $CaCl_2$, pH 7.4.

Step 2: C1q Binding and Washes
pH of the culture supernatant adjusted to 7;
washed immune complexes (ICs) suspended in the supernatant (example: 800 ml of supernatant for 57 mg of ICs) in the presence of 2 mM $CaCl_2$ and incubation for 45 min at 0° C.;

removal of the supernatant by centrifugation (10 min, 10,000 rpm);
washing of the immune complexes with 30 ml of 20 mM Tris buffer, 120 mM NaCl, 2.5 mM $CaCl_2$, pH 7.4 (3 times).

Step 3: C1q Extractions
extraction of C1q with 50 mM Tris buffer, 0.7 M NaCl, pH 10 (2 extractions with 5 ml then 1 extraction with 2.5 ml);
analysis by SDS-(10%) polyacrylamide gel electrophoresis of the samples of the various steps (perfusate, washes, extractions) under non-reducing conditions;
pooling of the 3 extractions and dialysis against 50 mM Tris buffer, 150 mM NaCl, pH 7.4.

b) Chromatography on Anti-Peptide Resin
2.5 ml of anti-peptide M2 affinity gel resin (Sigma ref: A2220) are washed in 50 mM Tris buffer, 150 mM NaCl, pH 7.4, at 7.5 ml/h (5 column volumes);
3 sequential washes with 1 column volume of 0.1 M glycine, pH 3.5;
washing with 5 volumes of 50 mM Tris buffer, 150 mM NaCl, pH 7.4;
loading of C1q extracted from the immune complexes in a "loop" overnight at 7.5 ml/h, i.e. approximately 7 passes;
washes with 5 column volumes;
elution with 2×1 column volume with peptide at 100 µg/ml in 50 mM Tris buffer, 150 mM NaCl, pH 7.4;
analyses of the various fractions by 14%-gel electrophoresis under non-reducing conditions;
pooling of the fractions containing C1q;
dialysis against 50 mM triethanolamine HCl buffer, 145 mM NaCl, pH 7.4;
concentration (Amicon Ultra cell with a cut-off threshold at 30 kDa) until a concentration of 0.4-0.5 mg/ml is reached.

Figure 2:
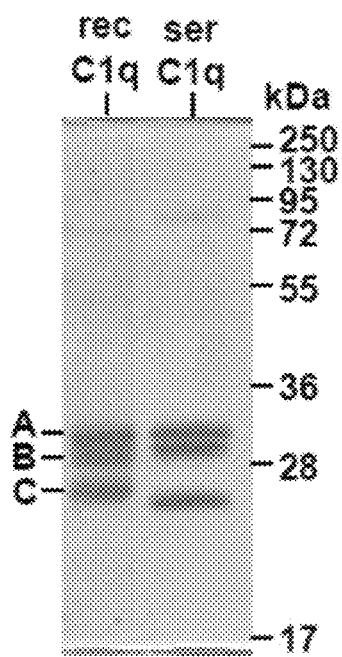
FIGS. 2 and 3 represent the analysis, by SDS-polyacrylamide gel electrophoresis, of recombinant C1q according to the invention (rec) and C1q derived from serum (ser) under reducing conditions (FIG. 2) and non-reducing conditions (FIG. 3).

5. Characterization of the Purified Recombinant Protein
a) Analysis by Polyacrylamide Gel Electrophoresis in the Presence of SDS Under reducing conditions (FIG. 2): the 3 chains A, B and C+peptide are obtained. It is clearly verified that the latter migrates more slowly than the C chain of C1q derived from serum owing to a slightly higher mass.

Figure 3:
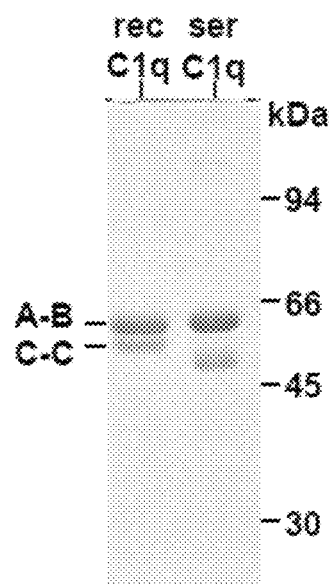

Under non-reducing conditions (FIG. 3): 2 bands are obtained, corresponding to C—C and A-B.

b) N-terminal Sequencing

Analysis after transfer onto PVDF membrane:
chain A: Glu-Asp-Leu-(Cys)-Arg-Ala-Pro
chain B: N-terminal glutamine blocked by formation of a pyroglutamate ring, as described for C1q derived from human serum by Reid & Thompson (1978) *Biochem. J.* 173:863-868)
chain C: Asn-Thr-Gly-(Cys)-Tyr-Gly-Ile-Pro b) Characterization by Mass Spectrometry
Chain A: 27278±10 Da
Chain B: 25497±55 Da
Chain C: 24898±164 Da The masses of the three recombinant chains appear to be the same order of magnitude as those of their homologs derived from serum C1q, given the addition of the peptide to the C chain, and therefore appear to comprise the post-translational glycosylation and hydroxylation modifications.

c) Characterization by Electron Microscopy

Figure 4:
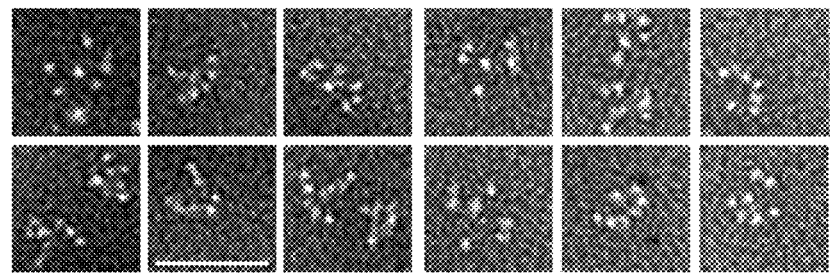
FIGS. 4 and 5 represent the analysis, by electron microscopy, of recombinant C1q according to the invention after negative staining with 2% sodium silicotungstate (FIG. 4) or with 2% ammonium molybdate (FIG. 5). The white bars represent 20 nm.
Figure 5:
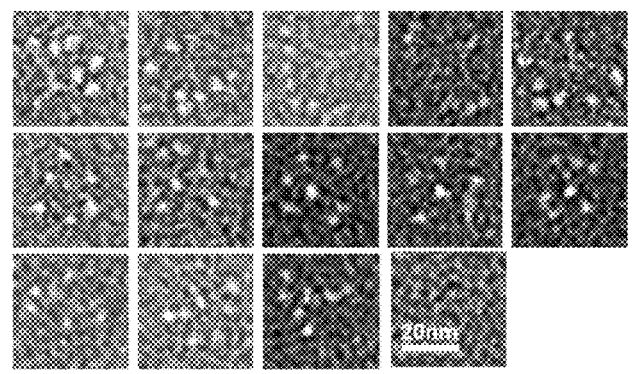

FIGS. 4 and 5 represent respectively the analysis by electron microscopy of recombinant C1q according to the invention after negative staining with 2% sodium silicotungstate and with 2% ammonium molybdate. The characteristic bouquet-of-tulips structure is clearly visible in the two cases.

d) Interaction Properties (Analysis by Surface Plasmon Resonance)

Figure 6:
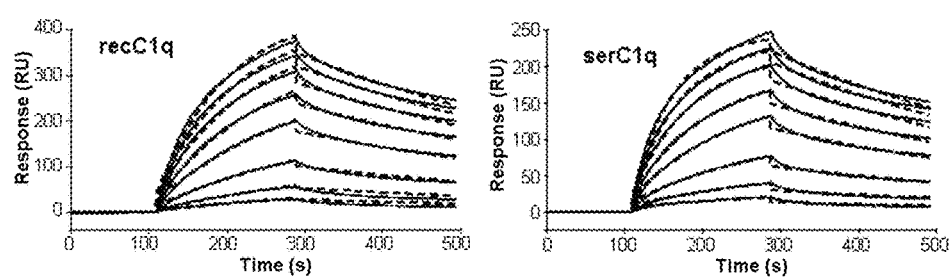
FIGS. 6 and 7 represent the response, measured by surface plasmon resonance (y-axis, in resonance units (RU)), to bringing immobilized recombinant C1q and immobilized serum C1q into contact with variable concentrations of the C1s-C1r-C1r-C1s tetramer (1, 2, 4, 8, 12, 16, 20 and 24 nM) (FIG. 6) or of human IgGs (12.5, 25, 50, 100, 150 and 200 nM) (FIG. 7) as a function of time (x-axis, in seconds). The experimental curves are in solid lines and the adjusted curves in dashed lines.
Figure 7:
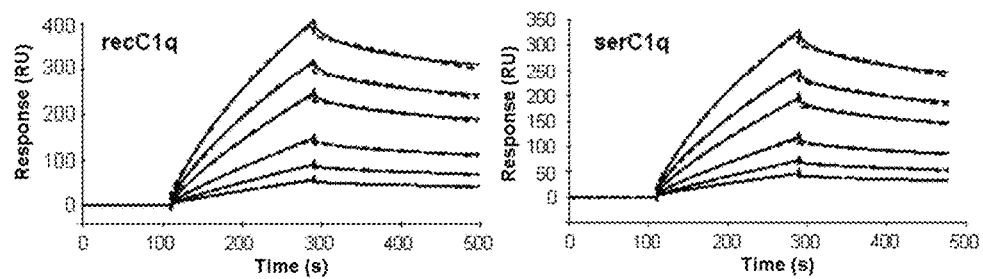

Recombinant C1q and serum C1q were immobilized on a CM5 sensorchip (GE Healthcare) and variable concentrations of the C1s-C1r-C1r-C1s tetramer (1, 2, 4, 8, 12, 16, 20 and 24 nM) (FIG. 6) or of human IgGs (12.5, 25, 50, 100, 150 and 200 nM) (FIG. 7) were injected at the surface thereof.

Similar reactivities are observed for the recombinant form and the serum form.

This is confirmed by the association and dissociation kinetic constants, calculated using the Biaeval software (GE Healthcare) and presented in Table 4 below:

| C1r2-C1s2 | recC1q | serC1q | IgG | recC1q | serC1q |
|---|---|---|---|---|---|
| $k_a$ (M$^{-1}$ s$^{-1}$) | 6.07 10$^5$ | 6.81 10$^5$ | $K_a$ (M$^{-1}$ s$^{-1}$) | 1.92 10$^4$ | 1.95 10$^4$ |
| $k_d$ (s$^{-1}$) | 1.96 10$^{-3}$ | 2.12 10$^{-3}$ | $k_d$ (s$^{-1}$) | 1.05 10$^{-3}$ | 1.2 10$^{-3}$ |
| $K_D$ (nM) | 3.22 | 3.12 | $K_D$ (nM) | 54.7 | 61.3 | e) Autoactivation Properties

Figure 8:
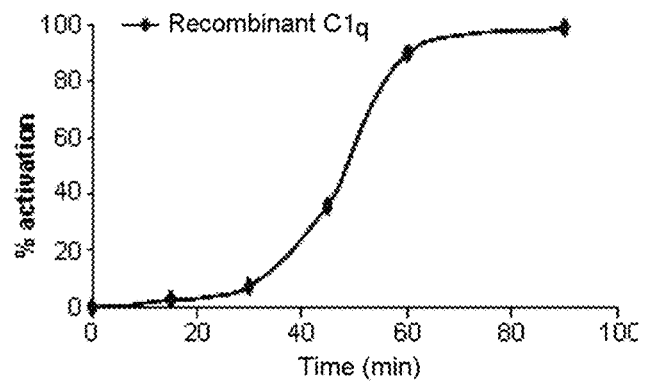
FIG. 8 represents the percentage activation of the C1s subunit (y-axis) as a function of time (x-axis, in minutes) in the C1 complex reconstituted from recombinant C1q according to the invention and the C1s-C1r-C1r-C1s proenzyme tetramer.

The C1 complex is reconstituted from C1q and from the C1s-C1r-C1r-C1s proenzyme tetramer. Incubation of the reconstituted complex at 37° C. leads to autoactivation of C1r which, in turn, activates C1s. The activation of C1s is measured by SDS-polyacrylamide gel electrophoresis under reducing conditions, followed by transfer onto a nitrocellulose membrane and immunovisualization with an anti-C1s antibody. The results are presented in FIG. 8.

It is observed that recombinant C1q displays an activation curve similar to that usually obtained for serum C1q.

Example 2

1. Cloning of Two Other C1qC Chains Modified by Addition of an Additional Amino Acid Sequence N-terminal Insertion of the DYKDDDDK Sequence (SEQ ID No. 8)

The DYKDDDDK sequence (SEQ ID No. 8) was inserted at the N-terminal end of the C1qC subunit by site-directed mutagenesis using the Quickchange kit (Agilent) so as to form the peptide+C1qC subunit.

Briefly, an amplification of the pcDNA3.1.C1qC plasmid is carried out by PCR using two complementary primers which incorporate the additional amino acid sequence to be inserted and which bind respectively to the two strands of the plasmid. For this, a reaction mixture comprising 200 ng of the pcDNA3.1.C1qC plasmid and 225 ng of an oligonucleotide having the sequence CCCCTCAGGGGCCAAGCC GATTACAAGGATGACGACGATAAGAACACAGGCT GC TACGGG (SEQ ID No. 18) and of an oligonucleotide having the sequence CCCGTAGCAGCCTGTGTT CTTATCGTCGTCATCCTTGTAATCGGCTTGGCCCCT GA GGGG (SEQ ID No. 19) is prepared (the underlined parts correspond to the sequence of the peptide to be inserted). 5 µl of Quick solution, 1 µl of dNTP mix and 1 µl of Pfu Turbo DNA polymerase (2.5 U/µl) (Agilent) are added to the mixture before amplification.

The amplification is then carried out under the following conditions:

| Cycle 1 | 95° C. | 1 min |
| Cycle 2 | 95° C. | 50 sec |
| Cycle 3 | 60° C. | 50 sec |
| Cycle 4 | 68° C. | 12 min |
| Cycles 2 to 4 are repeated 18 times | | |
| Cycle 5 | 68° C. | 7 min |

Two consecutive treatments for 1 hour with 1 µl of DpnI nuclease (10 U/µl) are then carried out in order to destroy the pcDNA3.1.C1qC template plasmids, then 2 µl of the mixture are used to transform E. coli XL10 Gold bacteria (Agilent).

The plasmid DNA of the transformed bacteria resistant to zeocin is extracted and then screened by sequencing.

C-terminal Insertion of the 6His Sequence

The HHHHHH sequence (SEQ ID No. 20) was inserted at the C-terminal end of the C1qC subunit by site-directed mutagenesis using the Quickchange kit (Agilent) so as to form the C1qC+6His subunit.

Briefly, an amplification of the pcDNA3.1.C1qC plasmid is carried out by PCR using two complementary primers which incorporate the sequence encoding the 6His peptide to be inserted and which bind respectively to the two strands of the plasmid. For this, a reaction mixture comprising 200 ng of the pcDNA3.1.C1qC plasmid and 225 ng of an oligonucleotide having the sequence GCTCTTCCCCGAC CATCACCATCACCATCACTAGGAGTTCTGCAGATA TCC (SEQ ID No. 21) and of an oligonucleotide having the sequence GGATATCTGCAGAACTCCTA GTGATGGTGATGGTGATGGTCGGGGAAGAGC (SEQ ID No. 22) is prepared (the underlined parts correspond to the sequence of the 6 histidines to be inserted). 5 µl of Quick solution, 1 µl of dNTP mix and 1 µl of Pfu Turbo DNA polymerase (2.5 U/µl) (Agilent) are added to the mixture before amplification.

The PCR amplification, the treatment with DpnI, the transformation of the bacteria, and the extraction and screening of the plasmid DNA of the transformed bacteria resistant to zeocin are carried out under the conditions described above for peptide+C1qC.

The sequences of the two new C chains of C1q obtained are represented hereinafter:

peptide + C1qC (SEQ ID No. 23)

MDVGPSSLPHLGLKLLLLLLLLALRGQADYKDDDDKNTGCYGIPGMPGLP

GAPGKDGYDGLPGPKGEPGIPAIPGIRGPKGQKGEPGLPGHPGKNGPMGP

PGMPGVPGPMGIPGEPGEEGRYKQKFQSVFTVTRQTHQPPAPNSLIRFNA

VLTNPQGDYDTSTGKFTCKVPGLYYFVYHASHTANLCVLLYRSGVKVVTF

CGHTSKTNQVNSGGVLLRLQVGEEVWLAVNDYYDMVGIQGSDSVFSGFLL

FPD

C1qC + 6xHis (SEQ ID No. 24)

MDVGPSSLPHLGLKLLLLLLLLALRGQANTGCYGIPGMPGLPGAPGKDGY

DGLPGPKGEPGIPAIPGIRGPKGQKGEPGLPGHPGKNGPMGPPGMPGVPG

PMGIPGEPGEEGRYKQKFQSVFTVTRQTHQPPAPNSLIRFNAVLTNPQGD

-continued

YDTSTGKFTCKVPGLYYFVYHASHTANLCVLLYRSGVKVVTFCGHTSKTN

QVNSGGVLLRLQVGEEVWLAVNDYYDMVGIQGSDSVFSGFLLFPD<u>HHHHH</u>
<u>H</u>

The sequence of the additional amino acid sequence or of the 6His tag is underlined and the sequences of the mature chains (after cleavage of the signal peptide) are indicated in bold.

2. Stable Transfections of the 293 F Cells

Generation of Stable Lines Producing the 3 C1q Chains:

The same protocol as indicated in example 1 was used to transfect a stable line already producing the A and B chains with the DNA encoding each of the two new variants of the C chain (peptide+C1qC and C1qC+6His), and then to select the stable transfectants in the presence of the 3 antibiotics.

Figure 9:
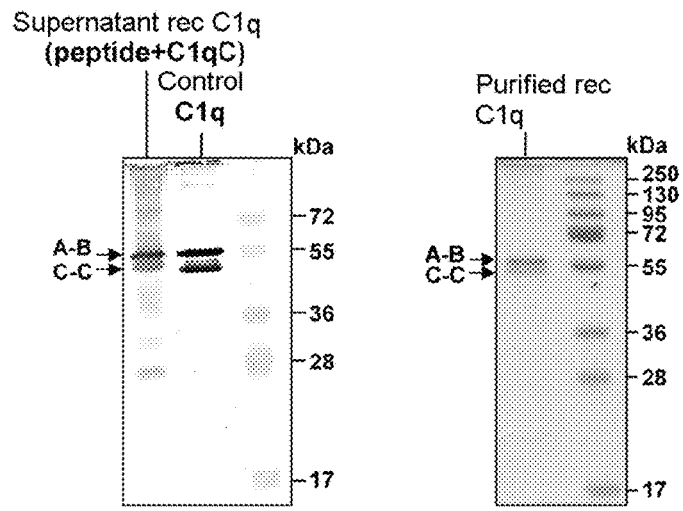
FIG. 9 The left-hand panel of FIG. 9 represents the analysis, by gel electrophoresis under non-reducing conditions and labeling of a Western blot with an anti-plasma C1q antibody, of the culture supernatant (1 ml) of recombinant C1q containing the chain peptide+C1qC. Control: 1.5 µg of plasma C1q.
The right-hand panel of FIG. 9 represents the analysis, by gel electrophoresis under non-reducing conditions, of purified recombinant C1q (4.8 µg) containing the chain peptide+C1qC.
Figure 10:
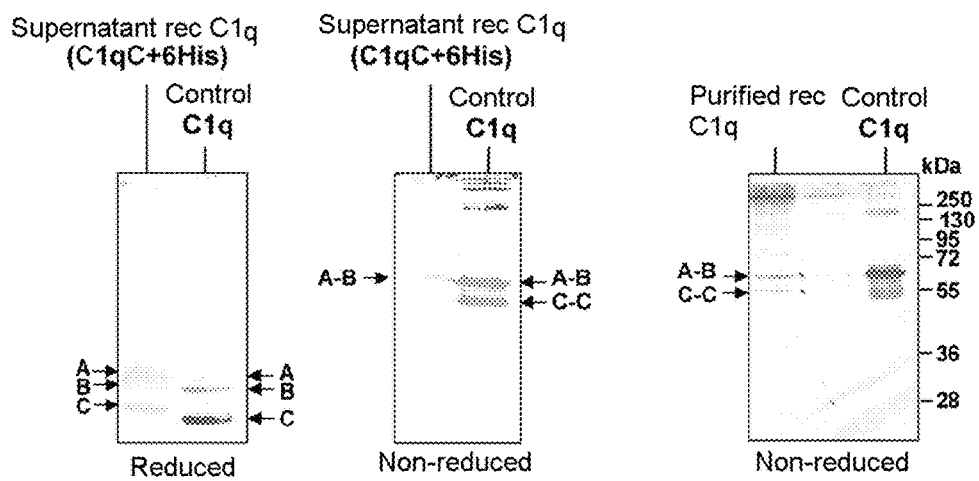
FIG. 10 represents the analysis, by gel electrophoresis and labeling of a Western blot with an anti-plasma C1q antibody, of the culture supernatant (2 ml) of recombinant C1q containing the chain C1qC+6His under reducing conditions (left-hand panel) and non-reducing conditions (center panel). Control: 2 µg of plasma C1q.
The right-hand panel of FIG. 10 represents the analysis, by gel electrophoresis under non-reducing conditions and labeling of a Western blot with an anti-plasma C1q antibody, of the whole of purified recombinant C1q containing the chain C1qC+6His.

The verification of the presence of the 3 chains is carried out by labeling of a Western blot with an anti-plasma C1q antibody (FIGS. 9 and 10). It may be noted that, in the case of recombinant C1q containing the C+6His chain, the three chains are detected in the culture supernatant under reducing conditions, but there is no evidence of presence of the C—C dimer under non-reducing conditions, which suggests incorrect folding of the protein. The C—C dimer is visible in the case of recombinant C1q containing the peptide+C1qC chain.

The inventors thus produced the following additional stable lines:

C1qAB+peptide+C1qC (AB+C) (concomitant transfection with pcDNA3.1.C1qA and pcDNA3.1.C1qB in a first step and then with peptide+C1qC in a second step).

C1qAB+C1qC+6His (AB+C) (concomitant transfection with pcDNA3.1.C1qA and pcDNA3.1.C1qB in a first step and then with C1qC+6His in a second step).

3. Production of the Recombinant Protein

The two new stable lines obtained were cultured as described in example 1.

4. Purification

The recombinant C1q protein containing a C chain with the additional amino acid sequence in the N-terminal position (peptide+C1qC) was purified like the recombinant protein containing a C chain with the additional amino acid sequence in the C-terminal position (C1qC+peptide), in two steps (adsorption of the culture supernatant onto immune columns and chromatography on anti-peptide resin).

After purification from 470 ml of culture supernatant, 36 µg of purified recombinant C1q (FIG. 9) were obtained, which represents a yield of approximately 80 µg/liter, i.e. 10% of the amount obtained under the same conditions with recombinant C1q containing the C chain with the additional amino acid sequence in the C-terminal position (800 µg/liter).

The presence of the additional amino acid sequence in the N-terminal position of the C chain of C1q allows the production of recombinant C1q but leads to a decrease in the recombinant C1q production yield compared with the configuration in which the peptide is placed in the C-terminal position.

The recombinant C1q protein containing a C chain with a 6His tag in the C-terminal position (C1qC+6His) was purified in two steps:

Step 1: adsorption of the culture supernatant onto immune complexes (identical to that used for the protein with C1qC+peptide). The 3 extractions are pooled and dialyzed against a phosphate buffered saline (PBS) containing 10 mM imidazole. The amount of proteins extracted is very low.

Step 2: Affinity Chromatography on Immobilized Nickel Ions:

1.5 ml of HIS-Select HF Nickel Affinity Gel resin (Sigma ref: H0537) are washed in PBS+10 mM imidazole, the fractions extracted from the immune complexes are loaded, washing is carried out with 20 ml PBS+10 mM imidazole, elution is carried out in PBS+300 mM imidazole, all of the eluate is used for a Western blot labeling analysis with an anti-plasma C1q antibody (FIG. 10).

The amount obtained under these conditions from 500 ml of supernatant is less than 1 µg, which confirms the analysis of the culture supernatants under non-reducing conditions, revealing a minute amount of correctly folded material.

The vast majority of recombinant C1q produced with a 6His tag in the C-terminal position of the C1qC chain is not correctly folded.

Table of sequences:

| SEQ ID No.: | Description |
| --- | --- |
| 1 | C1qA peptide sequence without signal peptide |
| 2 | C1qA peptide sequence with signal peptide |
| 3 | C1qB peptide sequence without signal peptide |
| 4 | C1qB peptide sequence with signal peptide |
| 5 | C1qC peptide sequence without signal peptide |
| 6 | C1qC peptide sequence with signal peptide |
| 7 | C1qC peptide sequence with signal peptide and with the additional amino acid sequence |
| 8 | Additional amino acid sequence |
| 9 | C1qA PCR amplification primer |
| 10 | C1qA PCR amplification primer |
| 11 | C1qB PCR amplification primer |
| 12 | C1qB PCR amplification primer |
| 13 | C1qC PCR amplification primer |
| 14 | C1qC PCR amplification primer |
| 15 | PCR primer for site-directed mutagenesis of C1qC |
| 16 | PCR primer for site-directed mutagenesis of C1qC |
| 17 | Additional amino acid sequence |
| 18 | C1qC PCR amplification primer |
| 19 | C1qC PCR amplification primer |
| 20 | Six-histidine (6His) tag |
| 21 | C1qC PCR amplification primer |
| 22 | C1qC PCR amplification primer |
| 23 | C1qC peptide sequence with signal peptide and with the additional amino acid sequence on the N-terminal site |
| 24 | C1qC peptide sequence with signal peptide and with the 6His sequence on the C-terminal site |

The invention claimed is:

1. A method for recombinantly producing a C1q protein, or a C1q protein variant, comprising:

providing an in vitro culture of mammalian cells stably expressing a mature C1qA subunit having the sequence of SEQ ID NO: 1 or a sequence at least 80% identical to SEQ ID NO: 1 provided that it can form a C1q protein, a mature C1qB subunit having the sequence of SEQ ID NO: 3 or a sequence at least 80% identical to SEQ ID NO: 3 provided that it can form a C1q protein, and a mature C1qC subunit having the sequence of SEQ ID NO: 5 or a sequence at least 80% identical to SEQ ID NO: 5 provided that it can form a C1q protein, and in which at least one of the mature subunits also bears, at the C-terminal end, an additional amino acid sequence of DYKDDDDK (SEQ ID NO: 8) or of EQKLISEEDL (SEQ ID NO: 17); and recovering the recombinant C1q protein or C1q protein variant from the in vitro culture of cells by a process comprising at least one affinity purification step.

2. The method of claim 1, wherein the additional amino acid sequence is located at the C-terminal end of one of the mature C1q subunits.

3. The method of claim 1, wherein the additional amino acid sequence is located at the C-terminal end of the mature C1qC subunit.

4. The method as claimed in claim 1, wherein the C1q protein, or the C1q protein variant, is recovered from the culture supernatant.

5. The method as claimed in claim 3, wherein the C1q protein, or the C1q protein variant, is recovered from the culture supernatant.

* * * * *